(12) United States Patent
Chang et al.

(10) Patent No.: US 11,339,131 B2
(45) Date of Patent: May 24, 2022

(54) PROCESS FOR PREPARING ELAGOLIX SODIUM AND INTERMEDIATES THEREOF

(71) Applicant: ScinoPharm Taiwan, Ltd., Tainan (TW)

(72) Inventors: Yung-Hung Chang, Tainan (TW); Tsung-Yu Hsiao, Tainan (TW); Yuan-Xiu Liao, Tainan (TW); Hsin-Chang Tseng, Tainan (TW)

(73) Assignee: ScinoPharm Taiwan, Ltd., Tainan (TW)

( * ) Notice: Subject to any disclaimer, the term of this patent is extended or adjusted under 35 U.S.C. 154(b) by 0 days.

(21) Appl. No.: 17/023,636

(22) Filed: Sep. 17, 2020

(65) Prior Publication Data

US 2021/0078956 A1 Mar. 18, 2021

Related U.S. Application Data

(60) Provisional application No. 62/902,086, filed on Sep. 18, 2019.

(51) Int. Cl.
*C07D 239/54* (2006.01)

(52) U.S. Cl.
CPC .................................. *C07D 239/54* (2013.01)

(58) Field of Classification Search
CPC .................................................... C07D 239/54
See application file for complete search history.

(56) References Cited

U.S. PATENT DOCUMENTS

| | | | | |
|---|---|---|---|---|
| 7,056,927 B2 * | 6/2006 | Guo | ..................... | C07D 239/54 514/274 |
| 8,765,948 B2 * | 7/2014 | Gallagher | ................ | A61P 15/00 544/311 |

FOREIGN PATENT DOCUMENTS

| | | |
|---|---|---|
| WO | 2011/146954 | 12/2011 |
| WO | 2017/221144 A1 | 12/2017 |
| WO | 2018/198086 | 11/2018 |
| WO | 2018/224063 A1 | 12/2018 |
| WO | 2019/112968 | 6/2019 |
| WO | 2019/115019 A1 | 6/2019 |

OTHER PUBLICATIONS

International Search Report and Written Opinion received in corresponding application PCT/SG2020/050530 dated Dec. 24, 2020 (16 pages).

* cited by examiner

*Primary Examiner* — D Margaret M Seaman
(74) *Attorney, Agent, or Firm* — Mintz Levin Cohn Ferris Glovsky and Popeo, P.C.

(57) ABSTRACT

The present invention provides improved processes for the preparation of elagolix and intermediates thereof. The intermediate of formula VII is achieved by a coupling reaction of a compound of formula V and a N-benzylidene protected compound of formula IV:

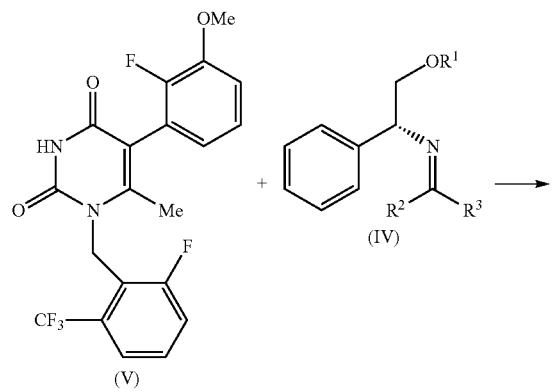

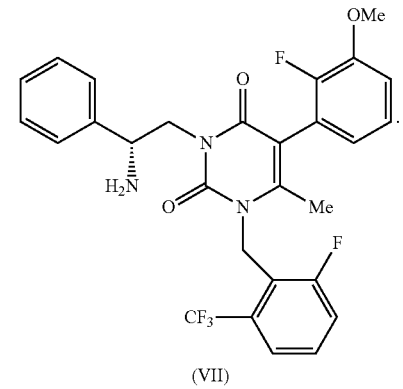

The present invention is suitable for a large-scale production, avoiding the use of potential genotoxic substances and can be performed under mild conditions.

22 Claims, 4 Drawing Sheets

FIG. 1

Scheme 1

Elagolix Sodium

Scheme 3

FIG. 4

PROCESS FOR PREPARING ELAGOLIX SODIUM AND INTERMEDIATES THEREOF

CROSS-REFERENCES TO RELATED APPLICATIONS

This application claims priority to U.S. Provisional Application No. 62/902,086 filed Sep. 18, 2019, which is incorporated in its entirety for all purpose.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Elagolix sodium (trade name Orilissa) is a gonadotropin-releasing hormone (GnRH) receptor antagonist indicated for the management of moderate to severe pain associated with endometriosis. Elagolix sodium is represented by the formula as shown below:

The chemical name of elagolix sodium is sodium 4-({(1R)-2-[5-(2-fluoro-3-methoxyphenyl)-3-{[2-fluoro-6-(trifluoromethyl)phenyl] methyl}-4-methyl-2,6-dioxo-3,6-dihydropyrimidin-1(2H)-yl]-1-phenylethyl}amino) butanoate. Elagolix sodium has a molecular formula of $C_{32}H_{29}F_5N_3O_5Na$ and a molecular weight of 653.58 Da.

Orilissa is the first FDA-approved oral pill specifically developed for women with moderate to severe endometriosis pain in over a decade.

Figure 1:
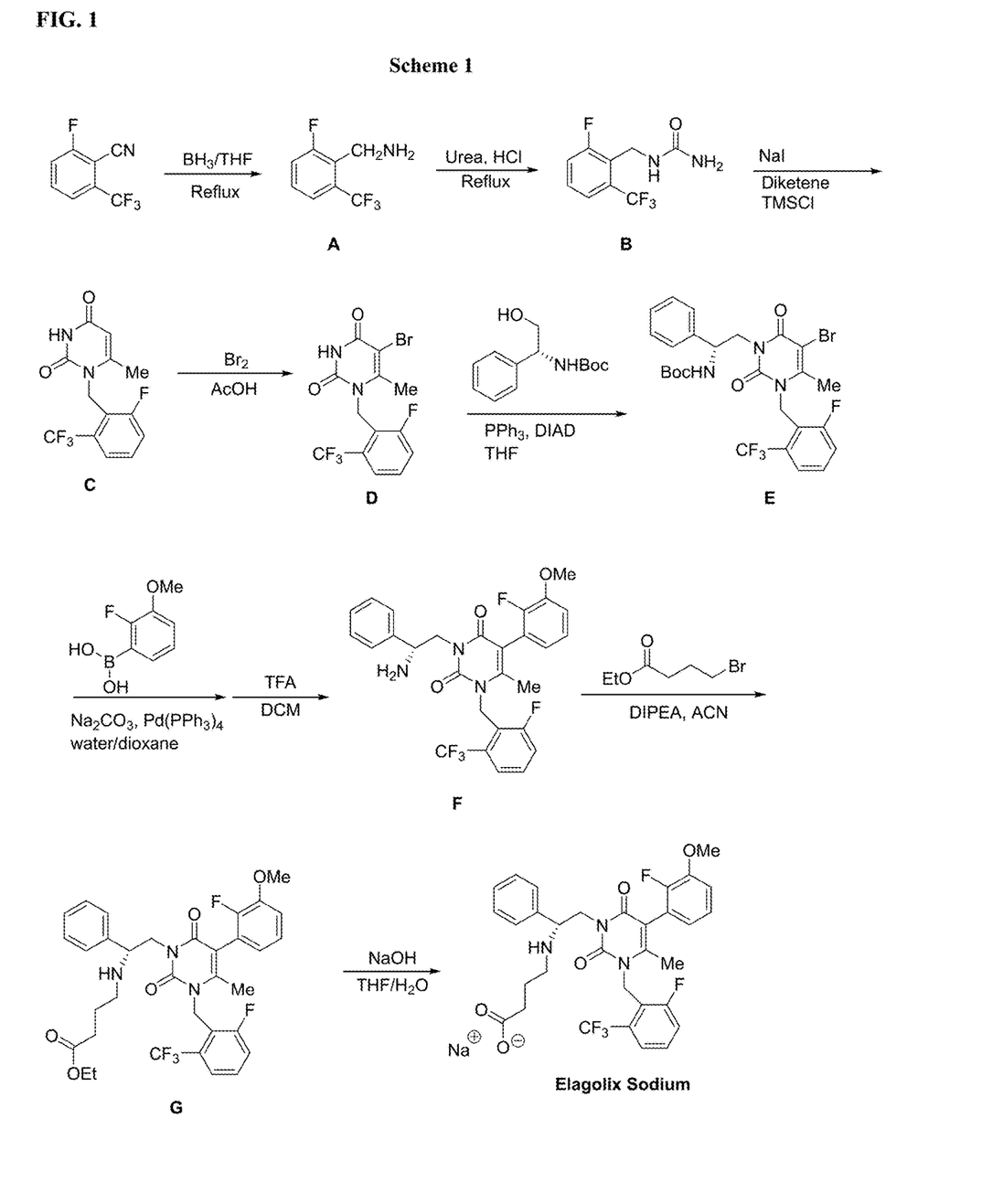
FIG. 1 shows the scheme for preparing elagolix sodium, as disclosed in U.S. Pat. No. 7,056,927 B2.

U.S. Pat. No. 7,056,927 B2 discloses the preparation of elagolix sodium as shown by Scheme 1 in FIG. 1. The preparation involved the construction of compound C from 2-fluoro-6-(trifluoromethyl)benzonitrile via an intramolecular cyclization, followed by introduction of Br at C5 position to give compound D. Compound D was alkylated with N-Boc-D-phenylglycinol at N3 position via a Mitsunobu reaction to afford compound E. Subsequently, compound E was reacted with 2-fluoro-3-methoxyphenylboronic acid in the presence of a Pd catalyst to undergo a Suzuki coupling reaction, followed by a de-Boc reaction to obtain compound F. The $NH_2$ group in compound F was alkylated with ethyl 4-bromobutyrate to give compound G. Finally, elagolix sodium was obtained by the hydrolysis of compound G with NaOH.

Figure 2:
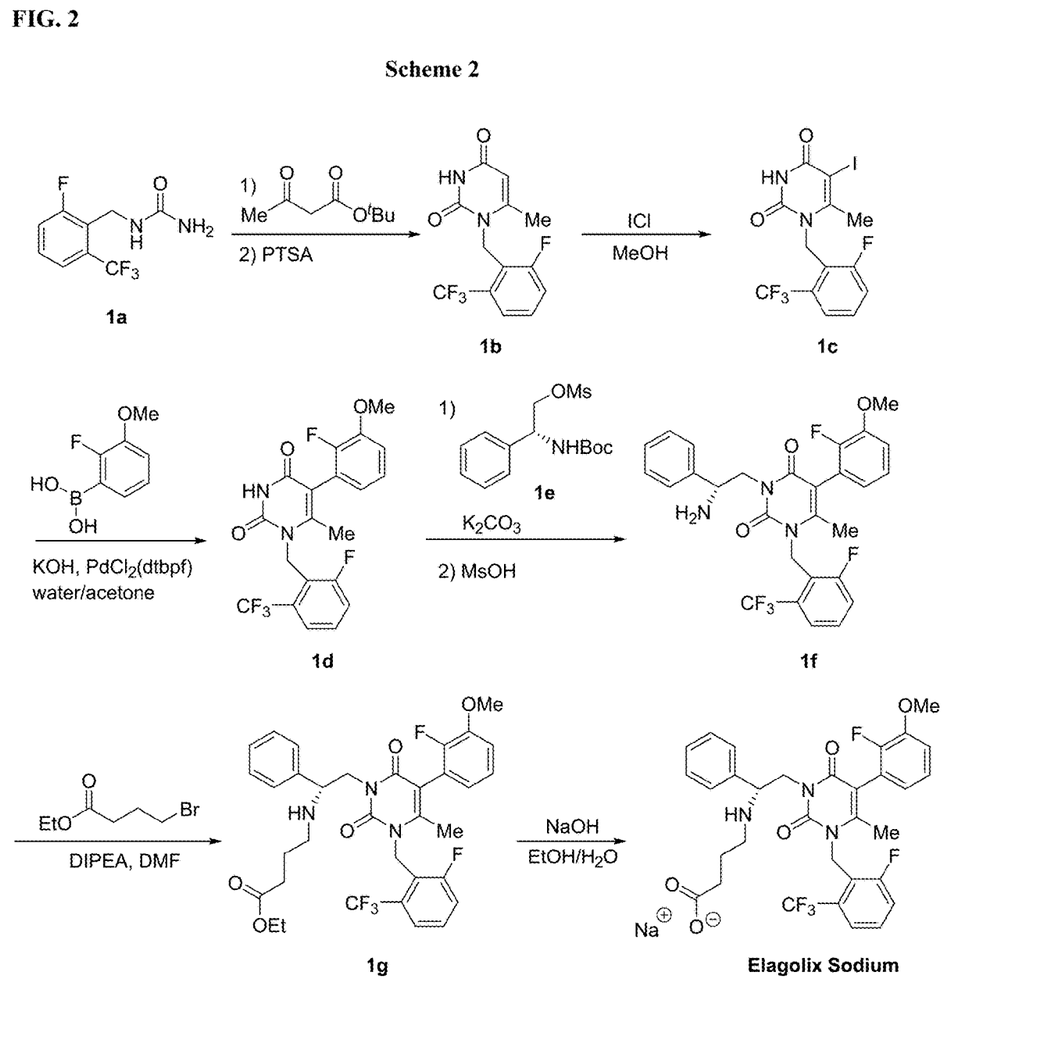
FIG. 2 shows the scheme of the first approach for preparing elagolix sodium, as disclosed in U.S. Pat. No. 8,765,948 B2.
Figure 3:
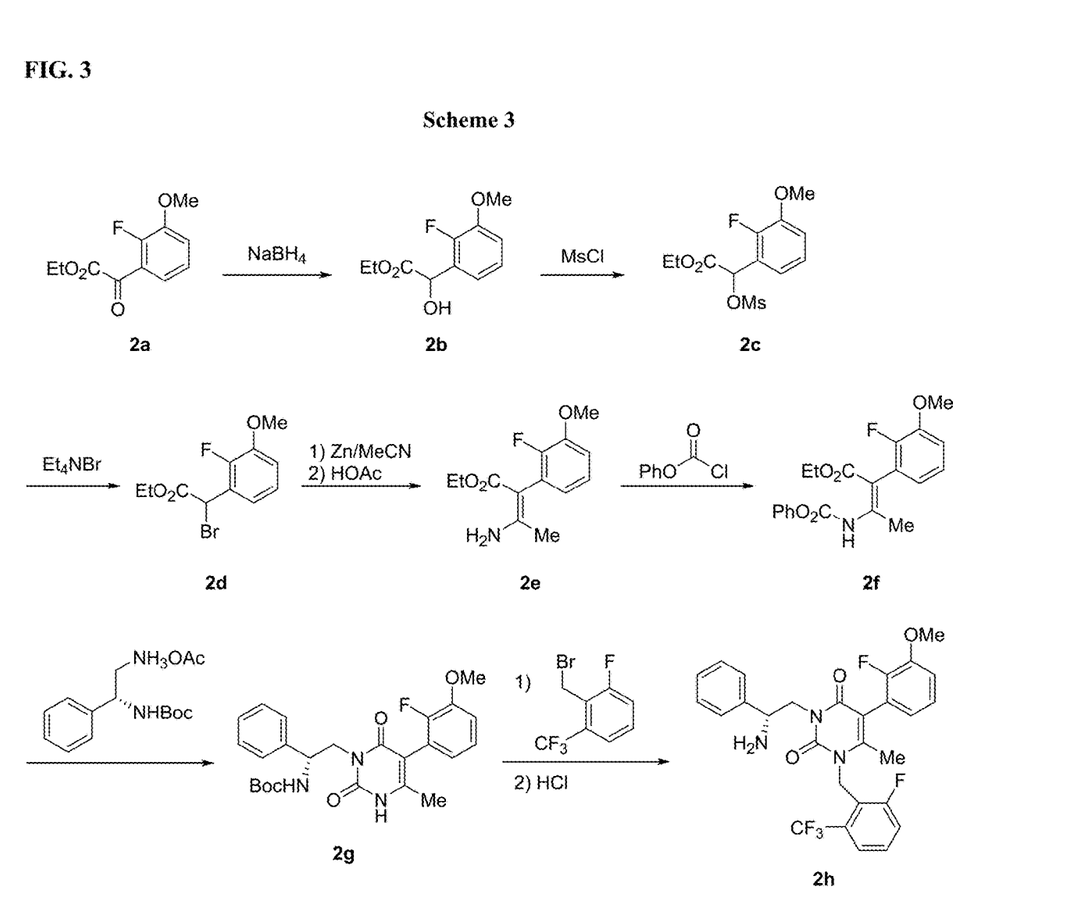
FIG. 3 shows the scheme of the second approach for preparing intermediates of elagolix sodium, as disclosed in U.S. Pat. No. 8,765,948 B2.

U.S. Pat. No. 8,765,948 B2 discloses two approaches for the general preparation of elagolix sodium and its intermediates, as shown by Scheme 2 in FIG. 2 and Scheme 3 in FIG. 3, respectively. As shown in FIG. 2, the first approach involved the introduction of iodo (I) instead of bromo (Br) at C5 position, followed by a Suzuki reaction with 2-fluoro-3-methoxyphenylboronic acid to give compound 1d. Compound 1f was obtained via the treatment of compound 1d with compound 1e under basic conditions, followed by de-Boc reaction. Subsequently, the $NH_2$ group in compound 1f was alkylated with ethyl 4-bromobutyrate to give compound 1g. After hydrolysis under basic conditions, elagolix sodium was obtained. As shown in FIG. 3, the second approach involved the construction of uracil derivative 2g from the reaction of compound 2f with t-Boc-(1R)-amino-2-amino-1-phenylethane acetate salt. Subsequently, compound 2g could be alkylated with 2-fluoro-6-trifluoromethylbenzyl bromide to give compound 2h. Compound 2h in Scheme 3 of FIG. 3 is also represented by compound F in Scheme 1 of FIG. 1 and compound 1f in Scheme 2 of FIG. 2.

Figure 4:
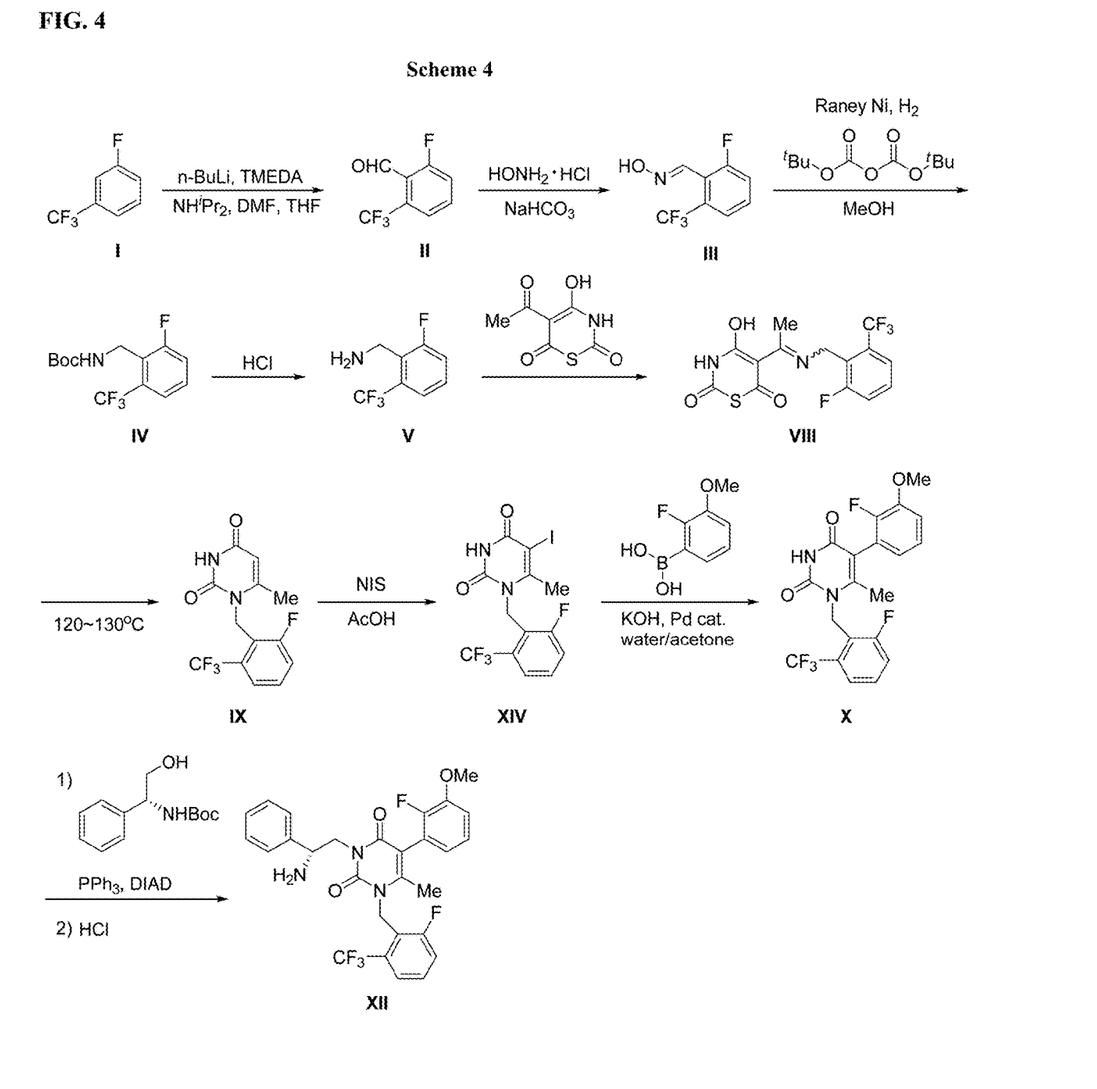
FIG. 4 shows the scheme for preparing intermediates of elagolix sodium, as disclosed in the PCT Publication No. WO 2019/112968 A1.

PCT Patent Application No. 2019/112968A1 discloses an alternative route for the preparation of elagolix and its intermediates, as shown by Scheme 4 in FIG. 4. In order to avoid the formation of potential genotoxic byproduct, such as methansulfonic acid, this route involved a Mitsunobu reaction to undergo a C—N bond coupling of compound X with N-Boc-D-phenylglycinol.

Despite the above described processes, there remains a need for the development of improved processes for the preparation of elagolix sodium. The present disclosure addresses this need and provides related advantages as well.

BRIEF SUMMARY OF THE INVENTION

In one aspect, the present invention provides a process for preparing a compound of formula VII:

or a salt thereof, the process including:
1) contacting a compound of formula V:

with a compound of formula IV:

(IV)

and one or more coupling agents in a first solvent to form a mixture; and
2) treating the mixture with an acid to provide the compound of formula VII or the salt thereof, wherein $R^1$ is hydrogen, methanesulfonate, or p-toluenesulfonate; and $R^2$ and $R^3$ are independently hydrogen, substituted or unsubstituted $C_{1-8}$ alkyl, or substituted or unsubstituted $C_{6-12}$ aryl.

In another aspect, the present invention provides a process for preparing elagolix of formula I:

(I)

or a pharmaceutically acceptable salt thereof, the process including:
1) contacting a compound of formula V:

(V)

with a compound of formula IV:

(IV)

and one or more coupling agents in a first solvent to form a mixture;

2) treating the mixture with an acid and neutralizing to provide a compound of formula VII:

(VII)

3) contacting the compound of formula VII with ethyl 4-halobutyrate and a third base in a fourth solvent to form a compound of formula VIII:

(VIII)

and 4) treating the compound of formula VIII with a fourth base in a fifth solvent to provide elagolix of formula I or the pharmaceutically acceptable salt thereof, wherein $R^1$ is hydrogen, methanesulfonate, or p-toluenesulfonate; and $R^2$ and $R^3$ are independently hydrogen, substituted or unsubstituted $C_{1-8}$ alkyl, or substituted or unsubstituted $C_{6-12}$ aryl.

DETAILED DESCRIPTION OF THE INVENTION

I. General

The present invention provides improved processes for the preparation of elagolix and intermediates thereof. As compared to prior art, the present invention is suitable for a large-scale production, avoiding the use of potential genotoxic substances and can be performed under mild conditions. The coupling reaction of the present invention utilizes N-benzylidene-D-phenylglycinol (the compound of formula IVa), in which the benzylidene group at the N atom has less steric hindrance than the tert-butoxycarbonyl (Boc) group of N-Boc-D-phenylglycinol. This steric difference is found to affect the ratio of N-alkylation/O-alkylation of the imide (the compound of formula V). When N-Boc-D-phenylglycinol (disclosed in WO 2019/112968 A1) is used, the reaction produces an O-alkylated side product in an amount of 8-10%. In the present invention, the O-alkylated side product is not observed when N-benzylidene-D-phenylglycinol is used. Furthermore, the deprotection of N-benzylidene group to generate the $NH_2$ group is achieved under mild conditions by treatment with an acid at room temperature. As comparison, the deprotection of the N-Boc group is performed at 60° C., as described in prior art.

II. Definitions

"Alkyl" refers to a straight or branched, saturated, aliphatic radical having the number of carbon atoms indicated (i.e., $C_{1-8}$ means one to eight carbons). Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-8}$ alkyl includes, but is not limited to, methyl, ethyl, n-propyl, isopropyl, n-butyl, isobutyl, sec-butyl, tert-butyl, n-pentyl, isopentyl, hexyl, heptyl, octyl, etc.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"OMs" refers to methanesulfonate; and "OTs" refers to p-toluenesulfonate.

"Salt" refers to acid or base salts of the compounds used in the methods of the present disclosure. Salts useful in the present disclosure include, but are not limited to, phosphate, sulfate, chloride, bromide, carbonate, nitrate, acetate, methanesulfonate, sodium, potassium, and calcium salts. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts, and alkaline metal or alkaline earth metal salts (sodium, potassium, calcium, and the like). It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

"Base" refers to a functional group that deprotonates water to produce a hydroxide ion. Bases useful in the present disclosure include organic bases and inorganic bases. Exemplary organic bases include tertiary amines, aromatic amine bases, and amidine-based compounds, as defined herein. Exemplary inorganic bases include alkali bicarbonates, alkali carbonates, and alkali hydroxides, as defined herein.

"First base", "second base", and so on refer to a base as defined above and described in embodiments of the present invention. The base naming conventions are used solely for the purpose of clarity in relevant steps of the process as described herein and they are not required to be in a numerical order. Some bases may be absent in selected embodiments of the present invention as described herein. One skilled in the art will understand the meaning of these base naming conventions ('first base', 'second base') within the context of the term's use in the embodiments and claims herein.

"Tertiary amine" refers to a compound having formula $N(R)_3$ wherein the R groups can be alkyl, aryl, heteroalkyl, heteroaryl, among others, or two R groups together form a N-linked heterocycloalkyl. The R groups can be the same or different. Non-limiting examples of tertiary amines include triethylamine, tri-n-butylamine, N,N-diisopropylethylamine, N-methylpyrrolidine, N-methylmorpholine, dimethylaniline, diethylaniline, 1,8-bis(dimethylamino)naphthalene, quinuclidine, and 1,4-diazabicylo[2.2.2]-octane (DABCO).

"Aromatic amine base" refers to a N-containing 5- to 10-membered heteroaryl compound or a tertiary amine having formula $N(R)_3$ wherein at least one R group is an aryl or heteroaryl. Aromatic amine bases useful in the present application include, but are not limited to, pyridine, lutidines (e.g., 2,6-lutidine, 3,5-lutidine, and 2,3-lutidine), collidines (e.g., 2,3,4-collidine, 2,3,5-collidine, 2,3,6-collidine, 2,4,5-collidine, 2,4,6-collidine, and 3,4,5-collidine), 4-dimethylaminopyridine, imidazole, dimethylaniline, and diethylaniline.

"Amidine-based compounds" herein refers to a class of chemical compounds that include, but are not limited to, 1,8-diazabicyclo[5.4.0]undec-7-ene (DBU) and 1,5-diazabicyclo[4.3.0]non-5-en (DBN).

"Alkali bicarbonate" refers to a class of chemical compounds which are composed of an alkali metal cation and the hydrogencarbonate anion ($HCO_3^-$). Alkali carbonates useful in the present disclosure include lithium bicarbonate ($LiHCO_3$), sodium bicarbonate ($NaHCO_3$), potassium bicarbonate ($KHCO_3$), and cesium bicarbonate ($CsHCO_3$).

"Alkali carbonate" refers to a class of chemical compounds which are composed of an alkali metal cation and the carbonate anion ($CO_3^{2-}$). Alkali carbonates useful in the present disclosure include lithium carbonate ($Li_2CO_3$), sodium carbonate ($Na_2CO_3$), potassium carbonate ($K_2CO_3$), and cesium carbonate ($Cs_2CO_3$).

"Alkali hydroxide" refers to a class of chemical compounds which are composed of an alkali metal cation and the hydroxide anion ($OH^-$). Alkali hydroxides useful in the present disclosure include lithium hydroxide (LiOH), sodium hydroxide (NaOH), potassium hydroxide (KOH), cesium hydroxide (CsOH), and calcium hydroxide ($Ca(OH)_2$).

"Contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

"Deprotecting" refers to remove the protecting group (e.g., the benzylidene group at the N-atom of a compound of formula VI) using one or more chemicals or agents so that the functional group (e.g., —NH$_2$ group) is restored to its original state.

"Solvent" refers to a substance, such as a liquid, capable of dissolving a solute. Solvents can be polar or non-polar, protic or aprotic. Polar solvents typically have a dielectric constant greater than about 5 or a dipole moment above about 1.0, and non-polar solvents have a dielectric constant below about 5 or a dipole moment below about 1.0. Protic solvents are characterized by having a proton available for removal, such as by having a hydroxy or carboxy group. Aprotic solvents lack such a group. Representative polar protic solvents include alcohols (methanol, ethanol, propanol, isopropanol, etc.), acids (formic acid, acetic acid, etc.) and water. Representative polar aprotic solvents include dichloromethane, chloroform, tetrahydrofuran, diethyl ether, acetone, ethyl acetate, dimethylformamide, dimethylacetamide, acetonitrile and dimethyl sulfoxide. Representative non-polar solvents include alkanes (pentanes, hexanes, etc.), cycloalkanes (cyclopentane, cyclohexane, etc.), benzene, toluene, diethyl ether, and 1,4-dioxane. Other solvents are useful in the present invention.

"First solvent", "second solvent", and so on refer to a solvent as defined above and described in embodiments of the present invention. The solvent naming conventions are used solely for the purpose of clarity in steps of the process as described herein and they are not required to be in a numerical order. Some solvents may be absent in selected embodiments of the present invention as described herein. One skilled in the art will understand the meaning of these solvent naming conventions (e.g., 'first solvent', 'second solvent') within the context of the term's use in the embodiments and claims herein.

III. DESCRIPTION OF EMBODIMENTS

In one aspect, the present invention provides a process for preparing a compound of formula VII:

or a salt thereof, the process including:
1) contacting a compound of formula V:

with a compound of formula IV:

and one or more coupling agents in a first solvent to form a mixture; and
2) treating the mixture with an acid to provide the compound of formula VII or the salt thereof, wherein R$^1$ is hydrogen, methanesulfonate, or p-toluenesulfonate; and R$^2$ and R$^3$ are independently hydrogen, substituted or unsubstituted C$_{1-8}$ alkyl, or substituted or unsubstituted C$_{6-12}$ aryl.

In some embodiments, the mixture includes a compound of formula VI:

In some embodiments, when R$^1$ is hydrogen, step 1) is conducted under Mitsunobu conditions.

In some embodiments, R$^1$ is hydrogen; R$^2$ and R$^3$ are independently hydrogen, substituted or unsubstituted C$_{1-8}$ alkyl, or substituted or unsubstituted C$_{6-12}$ aryl. In some embodiments, R$^1$ is hydrogen; R$^2$ is hydrogen; and R$^3$ is substituted or unsubstituted $C_{6-12}$ aryl. In some embodiments, $R^1$ is hydrogen; $R^2$ is hydrogen; and $R^3$ is phenyl. In some embodiments, $R^1$ is hydrogen; $R^2$ and $R^3$ are each substituted or unsubstituted $C_{1-8}$ alkyl. In some embodiments, $R^1$ is hydrogen; $R^2$ and $R^3$ are each methyl. In some embodiments, $R^1$ is hydrogen; $R^2$ is substituted or unsubstituted $C_{1-8}$ alkyl; and $R^3$ is substituted or unsubstituted $C_{6-12}$ aryl. In some embodiments, $R^1$ is hydrogen; $R^2$ is methyl; and $R^3$ is phenyl.

Mitsunobu conditions include an azodicarboxylate compound and triphenylphosphine. In some embodiments, the one or more coupling agents in step 1) are a combination of diethyl azodicarboxylate (DEAD) and triphenylphosphine, a combination of diisopropyl azodicarboxylate (DIAD) and triphenylphosphine, a combination of tetraisopropylazodicarboxamide (TIPA) and triphenylphosphine, a combination of azodicarbonyldipiperidine (ADDP) and triphenylphosphine, or a combination of bis(2,2,2-trichloroethyl) azodicarboxylate (TCEAD) and triphenylphosphine. In some embodiments, the one or more coupling agents in step 1) are a combination of diethyl azodicarboxylate (DEAD) and triphenylphosphine or a combination of diisopropyl azodicarboxylate (DIAD) and triphenylphosphine. In some embodiments, the one or more coupling agents in step 1) are a combination of diisopropyl azodicarboxylate (DIAD) and triphenylphosphine.

The first solvent under Mitsunobu conditions can be an aprotic solvent or a non-polar solvent, as defined herein. In some embodiments, the first solvent is dimethylformamide (DMF), dichloromethane (DCM), toluene, dimethylacetamide (DMAc), isopropyl acetate (IPAc), acetonitrile, tetrahydrofuran (THF), or mixtures thereof. In some embodiments, the first solvent includes tetrahydrofuran (THF).

In general, the Mitsunobu reaction (i.e., step 1)) can be performed at any suitable temperature. In some embodiments, the Mitsunobu reaction is conducted at a temperature of from 0° C. to 50° C. In some embodiments, the Mitsunobu reaction is conducted at a temperature of from 15° C. to 30° C. In some embodiments, the Mitsunobu reaction is conducted at room temperature.

In some embodiments, when $R^1$ is methanesulfonate (Ms) or p-toluenesulfonate (Ts), step 1) is conducted under nucleophilic conditions.

In some embodiments, $R^1$ is methanesulfonate (Ms); $R^2$ and $R^3$ are independently hydrogen, substituted or unsubstituted $C_{1-8}$ alkyl, or substituted or unsubstituted $C_{6-12}$ aryl. In some embodiments, $R^1$ is methanesulfonate (Ms); $R^2$ is hydrogen; and $R^3$ is substituted or unsubstituted $C_{6-12}$ aryl. In some embodiments, $R^1$ is methanesulfonate (Ms); $R^2$ is hydrogen; and $R^3$ is phenyl. In some embodiments, $R^1$ is methanesulfonate (Ms); $R^2$ and $R^3$ are each substituted or unsubstituted $C_{1-8}$ alkyl. In some embodiments, $R^1$ is methanesulfonate (Ms); $R^2$ and $R^3$ are each methyl. In some embodiments, $R^1$ is methanesulfonate (Ms); $R^2$ is substituted or unsubstituted $C_{1-8}$ alkyl; and $R^3$ is substituted or unsubstituted $C_{6-12}$ aryl. In some embodiments, $R^1$ is methanesulfonate (Ms); $R^2$ is methyl; and $R^3$ is phenyl.

In some embodiments, $R^1$ is p-toluenesulfonate (Ts); $R^2$ and $R^3$ are independently hydrogen, substituted or unsubstituted $C_{1-8}$ alkyl, or substituted or unsubstituted $C_{6-12}$ aryl. In some embodiments, $R^1$ is p-toluenesulfonate (Ts); $R^2$ is hydrogen; and $R^3$ is substituted or unsubstituted $C_{6-12}$ aryl. In some embodiments, $R^1$ is p-toluenesulfonate (Ts); $R^2$ is hydrogen; and $R^3$ is phenyl. In some embodiments, $R^1$ is p-toluenesulfonate (Ts); $R^2$ and $R^3$ are each substituted or unsubstituted $C_{1-8}$ alkyl. In some embodiments, $R^1$ is p-toluenesulfonate (Ts); $R^2$ and $R^3$ are each methyl. In some embodiments, $R^1$ is p-toluenesulfonate (Ts); $R^2$ is substituted or unsubstituted $C_{1-8}$ alkyl; and $R^3$ is substituted or unsubstituted $C_{6-12}$ aryl. In some embodiments, $R^1$ is p-toluenesulfonate (Ts); $R^2$ is methyl; and $R^3$ is phenyl.

The nucleophilic conditions include a first base. In some embodiments, the one or more coupling agents in step 1) are a first base. The first base can be an organic or inorganic base, as defined herein. In some embodiments, the first base is an inorganic base. In some embodiments, the first base is an alkali carbonate. In some embodiments, the first base is lithium carbonate ($Li_2CO_3$), sodium carbonate ($Na_2CO_3$), potassium carbonate ($K_2CO_3$), and cesium carbonate ($Cs_2CO_3$), or combinations thereof. In some embodiments, the first base is potassium carbonate ($K_2CO_3$).

The first solvent under nucleophilic conditions can be an aprotic solvent or a non-polar solvent as defined herein. In some embodiments, the first solvent is dimethylformamide (DMF), dichloromethane (DCM), toluene, dimethylacetamide (DMAc), isopropyl acetate (IPAc), acetonitrile, tetrahydrofuran (THF), or mixtures thereof. In some embodiments, the first solvent includes dimethylformamide (DMF).

In general, the nucleophilic reaction (i.e., step 1)) can be performed at any suitable temperature. In some embodiments, the nucleophilic reaction is conducted at a temperature of from 0° C. to 100° C. In some embodiments, the nucleophilic reaction is conducted at a temperature of from 20° C. to 70° C. In some embodiments, the nucleophilic reaction is conducted at a temperature of about 55° C.

In some embodiments, step 2) includes:
2a) treating the mixture with an acid in a second solvent to provide the salt of the compound of formula VII.

In some embodiments, step 2) includes:
2a) treating the mixture with an acid in a second solvent to provide the salt of the compound of formula VII; and
2b) neutralizing the salt of the compound of formula VII with a second base in a third solvent including water to provide the compound of formula VII.

In some embodiments, the acid is hydrochloric acid (HCl) or methanesulfonic acid. In some embodiments, the acid is an aqueous solution of HCl or methanesulfonic acid. In some embodiments, the acid is an aqueous solution of HCl. In some embodiments, the acid is methanesulfonic acid.

In some embodiments, the salt of the compound of formula VII is a HCl salt thereof.

The second solvent for deprotection (i.e., step 2a)) can be an aprotic solvent or a non-polar solvent as defined herein. In some embodiments, the second solvent is dimethylformamide (DMF), dichloromethane (DCM), toluene, dimethylacetamide (DMAc), isopropyl acetate (IPAc), acetonitrile, tetrahydrofuran (THF), or mixtures thereof. In some embodiments, the second solvent includes toluene. In some embodiments, the second solvent includes isopropyl acetate (IPAc).

In general, the deprotection reaction (i.e., step 2a)) can be performed at any suitable temperature. In some embodiments, the deprotection reaction is conducted at a temperature of from 0° C. to 80° C. In some embodiments, the deprotection reaction is conducted at a temperature of from 20° C. to 70° C. In some embodiments, when the acid is an aqueous solution of HCl, the deprotection reaction is conducted at a room temperature of from 15° C. to 30° C. In some embodiments, when the acid is methanesulfonic acid, the deprotection reaction is conducted at a temperature of about 60° C.

The second base in step 2b) can be an inorganic base as defined herein. In some embodiments, the second base is an inorganic base. In some embodiments, the second base is an alkali carbonate. In some embodiments, the second base is sodium carbonate ($Na_2CO_3$) or potassium carbonate ($K_2CO_3$). In some embodiments, the second base is potassium carbonate ($K_2CO_3$).

The third solvent for neutralization (i.e., step 2b)) can include water. In some embodiments, the third solvent includes water. In some embodiments, the neutralization step takes place in an aqueous solution including the salt of the compound of formula VII.

In general, the neutralization reaction (i.e., step 2b)) can be performed at any suitable temperature. In some embodiments, the neutralization reaction is conducted at a temperature of from 0° C. to 50° C. In some embodiments, the neutralization reaction is conducted at a temperature of from 15° C. to 30° C.

In some embodiments, steps 1) and 2) are conducted in one-pot. In some embodiments, steps 1) and 2a) are conducted in one-pot. In some embodiments, steps 1), 2a), and 2b) are conducted in one-pot. In some embodiments, the compound of formula VI is used directly in step 2) without isolation. In some embodiments, the compound of formula VI is used directly in step 2a) without isolation. In some embodiments, the salt of the compound of formula VII is used directly in step 2b) without isolation.

In some embodiments, the compound of formula VI is isolated prior to step 2). In some embodiments, the compound of formula VI is isolated prior to step 2a). In some embodiments, the salt of the compound of formula VII is isolated prior to step 2b).

In some embodiments, the present invention provides a process for preparing a compound of formula VII:

(VII)

the process including:
1) contacting a compound of formula V:

(V)

with a compound of formula IV:

(IV)

and one or more coupling agents in a first solvent to form a mixture;
2a) treating the mixture with an acid in a second solvent to provide a salt of the compound of formula VII; and
2b) neutralizing the salt of the compound of formula VII with a second base in a third solvent comprising water to provide the compound of formula VII,
wherein $R^1$, $R^2$, and $R^3$ are defined and described herein; and steps 1), 2a), and 2b) are described herein.

In some embodiments, the present invention provides a process for preparing a salt of a compound of formula VII:

(VII)

the process including:
1) contacting a compound of formula V:

(V)

with a compound of formula IV:

(IV)

and one or more coupling agents in a first solvent to form a mixture; and 2a) treating the mixture with an acid in a second solvent to provide the salt of the compound of formula VII, wherein $R^1$, $R^2$, and $R^3$ are defined and described herein; and steps 1) and 2a) are described herein.

In some embodiments, the mixture includes a compound of formula VI:

(VI)

In some embodiments, the salt of the compound of formula VII is a HCl salt thereof.

In another aspect, the present invention provides a process for preparing elagolix of formula I:

(I)

or a pharmaceutically acceptable salt thereof, the process including:

1) contacting a compound of formula V:

(V)

with a compound of formula IV:

(IV)

and one or more coupling agents in a first solvent to form a mixture;

2) treating the mixture with an acid and neutralizing to provide a compound of formula VII:

(VII)

3) contacting the compound of formula VII with ethyl 4-halobutyrate and a third base in a fourth solvent to form a compound of formula VIII:

(VIII)

and 4) treating the compound of formula VIII with a fourth base in a fifth solvent to provide elagolix of formula I or the pharmaceutically acceptable salt thereof, wherein $R^1$ is hydrogen, methanesulfonate, or p-toluenesulfonate; and $R^2$ and $R^3$ are independently hydrogen, substituted or unsubstituted $C_{1-8}$ alkyl, or substituted or unsubstituted $C_{6-12}$ aryl.

In some embodiments, the mixture includes a compound of formula VI:

In some embodiments, R', R², and R³ are described above.
In some embodiments, step 2) includes:
2a) treating the mixture with an acid in a second solvent to provide the salt of the compound of formula VII; and
2b) neutralizing the salt of the compound of formula VII with a second base in a third solvent comprising water to provide the compound of formula VII.

In some embodiments, steps 2a) and 2b) as described above.

In some embodiments, the salt of the compound of formula VII is a HCl salt thereof.

In some embodiments, the ethyl 4-halobutyrate in step 3) is ethyl 4-bromobutyrate.

The third base in step 3) can be an organic or inorganic base, as defined herein. In some embodiments, the third base is an organic base. In some embodiments, the third base is a tertiary amine. In some embodiments, the third base is triethylamine, tri-n-butylamine, N,N-diisopropylethylamine, N-methylpyrrolidine, N-methylmorpholine, dimethylaniline, or diethylaniline. In some embodiments, the third base is N,N-diisopropylethylamine (DIPEA).

The fourth solvent for step 3) can be an aprotic solvent or a non-polar solvent as defined herein. In some embodiments, the fourth solvent is dimethylformamide (DMF), dichloromethane (DCM), toluene, dimethylacetamide (DMAc), isopropyl acetate (IPAc), acetonitrile, tetrahydrofuran (THF), or mixtures thereof. In some embodiments, the fourth solvent includes dimethylacetamide (DMAc).

In general, step 3) can be performed at any suitable temperature. In some embodiments, the step 3) reaction mixture can be at a temperature of from 0° C. to 100° C. In some embodiments, the step 3) reaction mixture can be at a temperature of from 20° C. to 70° C. In some embodiments, the step 3) reaction mixture can be at a temperature of about 55° C.

The fourth base in step 4) can be an inorganic base as defined herein. In some embodiments, the fourth base is an alkali hydroxide. In some embodiments, the fourth base is sodium hydroxide (NaOH), potassium hydroxide (KOH), or calcium hydroxide (Ca(OH)₂). In some embodiments, the fourth base is sodium hydroxide (NaOH) or calcium hydroxide (Ca(OH)₂). In some embodiments, the fourth base is sodium hydroxide (NaOH).

The fifth solvent for step 4) can be an alcohol, water, or combinations thereof. In some embodiments, the fifth solvent includes ethanol and water.

In general, step 4) can be performed at any suitable temperature. In some embodiments, the step 4) reaction mixture is at a temperature of from 0° C. to 50° C. In some embodiments, the step 4) reaction mixture is at a temperature of from 15° C. to 30° C.

In some embodiments, the pharmaceutically acceptable salt of elagolix of formula I is a sodium salt. In some embodiments, the elagolix of formula I is elagolix sodium.

In some embodiments, steps 1) and 2) are conducted in one-pot. In some embodiments, steps 1) and 2a) are conducted in one-pot. In some embodiments, steps 1), 2a), and 2b) are conducted in one-pot. In some embodiments, the compound of formula VI is used directly in step 2) without isolation. In some embodiments, the compound of formula VI is used directly in step 2a) without isolation. In some embodiments, the salt of the compound of formula VII is used directly in step 2b) without isolation.

In some embodiments, the compound of formula VI is isolated prior to step 2). In some embodiments, the compound of formula VI is isolated prior to step 2a). In some embodiments, the salt of the compound of formula VII is isolated prior to step 2b).

In some embodiments, steps 3) and 4) are conducted in one-pot. In some embodiments, steps 1) to 4) are conducted in one-pot.

In some embodiments, elagolix sodium is isolated as a solid.

IV. Examples

Example 1: Preparation of the Compound of Formula III

To a suitable reactor, the compound of formula II (90.0 g) and acetic acid (900 mL) were added at room temperature. The resulting clear solution was added N-iodosuccinimide

(80.4 g). The mixture was heated to 50° C. and stirred for 8 hours. Upon completion, the suspension was added water (2250 mL) slowly and then cooled to room temperature. The slurry was stirred at room temperature for 2 hours, followed by filtration. The wet cake was washed with water (540 mL) twice and then dried in vacuo at 60° C. to afford crude compound of formula III. Crude compound of formula III and MeOH (225 mL) was charged to a suitable reactor. The slurry mixture was heated to reflux and stirred for 1 hour. After reflux, the slurry was cooled to room temperature and stirred for 1 hour, followed by filtration. The wet cake was washed with pre-cooled MeOH (90 mL) and then dried in vacuo at 60° C. to afford the compound of formula III (115.38 g, 90.5% yield).

Example 2: Preparation of the Compound of Formula V

To a suitable reactor, the compound of formula III (20.00 g), 2-fluoro-3-methoxyphenylboronic acid (10.29 g), acetone (22 mL) were charged. KOH (10.62 g) in water (76 mL) was added. The resulting mixture was degassed for 30 min. The mixture was heated to 40° C., followed by addition of $PdCl_2(dtbpf)$ (0.0432 g). The reaction was heated to 45° C. and stirred for 2.5 hrs. Upon completion, the reaction was cooled to room temperature. Celite (5.01 g) was added. The mixture was stirred for 1 hr, followed by filtration. The Celite cake was washed with a mixture solution of KOH (1.53 g)/acetone (10.4 mL)/water (30 mL). The filtrate was added slowly to another flask containing THF (60 mL)/AcOH (30.2 mL)/water (20 mL) at 60° C. After addition, the resulting slurry was cooled to room temperature and then stirred for 1 hr. The slurry was filtered through a Buchner funnel to afford a wet cake. The wet cake was washed with water/MeOH (v/v=⅔, 50 mL) twice, followed by MeOH (64 mL) twice. The wet cake was dried at NMT 50° C. in vacuo to give the compound of formula V (17.89 g, 88.4% yield).

Example 3: Preparation of the Compound of Formula VII

To a suitable reactor, the compound of formula V (5.00 g), N-benzylidene-D-phenylglycinol (4.63 g), $PPh_3$ (6.15 g) and THF (75 mL) were added, followed by addition of DIAD (4.74 g). The reaction was stirred at room temperature for 2 hours. Upon completion, the reaction was quenched with water (10 mL) and then stirred for 10 min. The resulting mixture concentrated via solvent-swap with toluene (30 mL) to 6 vol. 3N HCl (11.7 mL) was added. The resulting mixture was stirred at room temperature for 1 hour. Upon completion, MeOH (30 mL) was added. The solution was washed with n-heptane (30 mL) for three times, followed by concentration via solvent-swap with toluene to 6 vol. The solution was neutralized with $K_2CO_3$ (8.12 g) in water (42.5 mL). The aqueous layer was extracted with toluene (25 mL). The combined organic layers were extracted with 10%

H$_3$PO$_4$ (50 mL) twice. The aqueous layer was washed with IPAc (50 mL) twice. The aqueous layer was neutralized with K$_2$CO$_3$ (16.28 g) in water (25 mL). The resulting solution was extracted with IPAc (42.5 mL). The organic layer was washed with water (15 mL) and then recrystallized with IPAc/n-heptane to give the compound of formula VII (5.89 g, 92.2% yield).

Example 4: Preparation of the Compound of Formula VII

V

VII

To a suitable reactor, the compound of formula V (3.00 g), N-isopropylidene-D-phenylglycinol (2.54 g), PPh$_3$ (3.69 g) and THF (45 mL) were added, followed by addition of DIAD (2.90 g). The reaction was stirred at room temperature for 2 hours. Upon completion, the reaction was quenched with water (6 mL) and then stirred for 10 min. The resulting mixture concentrated via solvent-swap with toluene (18 mL) to 6 vol. MsOH (0.91 mL) was added. The resulting mixture was stirred at 60° C. for 1 hour. Upon completion, K$_2$CO$_3$ (3.89 g) in water (25.5 mL) was added at NMT 30° C. Toluene (15 mL) was added to the mixture for phase separation. The aqueous layer was extracted with toluene (15 mL). The combined organic layers were extracted with 10% H$_3$PO$_4$ (30 mL) twice. The combined aqueous layer was washed with IPAc (30 mL) twice. The aqueous layer was neutralized with K$_2$CO$_3$ (9.76 g) in water (15 mL). The resulting solution was extracted with IPAc (25.5 mL). The organic layer was washed with water (9 mL) and then recrystallized with IPAc/n-heptane to give the compound of formula VII (3.45 g, 89.9% yield).

Example 5: Preparation of the Compound of Formula VII

To a suitable reactor, the compound of formula V (3.00 g), [(2R)-2-[(E)-benzylideneamino]-2-phenyl-ethyl] methanesulfonate (3.44 g), K$_2$CO$_3$ (2.43 g) and DMF (20 mL) were added. The reaction was stirred at 55° C. Upon completion, IPAc (24 mL) and water (28.5 mL) were charged to the reactor. The organic layer was washed with water (16 mL). 3N HCl (0.78 mL) was added. The resulting mixture was stirred at room temperature for 1 hour. Upon completion, MeOH (18 mL) was added. The solution was washed with n-heptane (18 mL) for three times, followed by concentration via solvent-swap with toluene to 6 vol. The solution was neutralized with K$_2$CO$_3$ (4.87 g) in water (25.5 mL). The aqueous layer was extracted with toluene (15 mL). The combined organic layers were extracted with 10% H$_3$PO$_4$ (30 mL) twice. The aqueous layer was washed with IPAc (30 mL) twice. The aqueous layer was neutralized with K$_2$CO$_3$ (9.77 g) in water (15 mL). The resulting solution was extracted with IPAc (25.5 mL). The organic layer was washed with water (9 mL) and then recrystallized with IPAc/n-heptane to give the compound of formula VII (3.23 g, 84.1% yield).

Example 6: Preparation of the Compound of Formula VIII and Elagolix Sodium

To a suitable reactor, the compound of formula VII (3.00 g), ethyl 4-bromobutyrate (0.95 mL) and DMAc (4.5 mL) were added. DIPEA (1.25 mL) was added. The resulting mixture was heated to 55° C. overnight. Upon completion, the reaction was cooled to room temperature. IPAc (15 mL) and water (9 mL) were added. The resulting mixture was stirred for 10 min. The organic layer was washed with citric acid (0.31 g) in water (6 mL). The organic layer was extracted with 85% $H_3PO_4$ (1.07 g) in water (21 mL), followed by 85% $H_3PO_4$ (0.44 g) in water (6 mL). The combined phosphoric acid layers were washed with IPAc (6 mL) twice. IPAc (15 mL) was added to the aqueous solution. The mixture was neutralized with $K_2CO_3$ (3.05 g) in water (4.5 mL). The organic layer was solvent-swapped with EtOH (15 mL) to afford the compound of formula VIII in EtOH solution. NaOH (0.44 g) in water (6 mL) was added slowly. The resulting mixture was stirred at room temperature for 2 hours. Upon completion, water (9 mL) was added. The solution was concentrated to 5 vol. water (15 mL) and MIBK (9 mL) were added. The mixture was agitated, and then separated. MIBK (9 mL) was added to the aqueous layer. The resulting mixture was concentrated to 10 vol, followed by addition of NaCl (4.5 g) and MIBK (21 mL). The resulting mixture was stirred at 25-30° C., followed by phase separation. The organic layer was concentrated to 3 vol. The resulting suspension was filtered to remove residual NaCl solids. The filtrate was added to a well-agitated n-heptane solution (30 mL). The suspension was stirred for 2 hours. The suspension was filtered through a Buchner funnel, followed by washing with n-heptane (6 mL). The wet cake was dried at 70° C. in vacuo to give elagolix sodium (2.39 g, 66.5% yield).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A process for preparing elagolix of formula I:

or a pharmaceutically acceptable salt thereof, the process comprising:

1) contacting a compound of formula V:

with a compound of formula IV:

and one or more coupling agents in a first solvent to form a mixture;

2) treating the mixture with an acid and neutralizing to provide a compound of formula VII:

(VII)

3) contacting the compound of formula VII with ethyl 4-halobutyrate and a third base in a fourth solvent to form a compound of formula VIII:

(VIII)

and 4) treating the compound of formula VIII with a fourth base in a fifth solvent to provide elagolix of formula I or the pharmaceutically acceptable salt thereof, wherein $R^1$ is hydrogen;

$R^2$ and $R^3$ are independently hydrogen, substituted or unsubstituted $C_{1-8}$ alkyl, or substituted or unsubstituted $C_{6-12}$ aryl;

the one or more coupling agents in step 1) are a combination of diethyl azodicarboxylate (DEAD) and triphenylphosphine, a combination of diisopropyl azodicarboxylate (DIAD) and triphenylphosphine, a combination of tetraisopropylazodicarboxamide (TIPA) and triphenylphosphine, a combination of azodicarbonyldipiperidine (ADDP) and triphenylphosphine, or a combination of bis(2,2,2-trichloroethyl) azodicarboxylate (TCEAD) and triphenylphosphine; and the first solvent in step 1) is dimethylformamide (DMF), dichloromethane (DCM), toluene, dimethylacetamide (DMAc), isopropyl acetate (IPAc), acetonitrile, tetrahydrofuran (THF), or mixtures thereof.

2. The process of claim 1, wherein the mixture comprises a compound of formula VI:

(VI)

3. The process of claim 1, wherein $R^2$ is hydrogen and $R^3$ is phenyl, or $R^2$ and $R^3$ are each methyl.

4. The process of claim 3, wherein the one or more coupling agents in step 1) are a combination of diethyl azodicarboxylate (DEAD) and triphenylphosphine or a combination of diisopropyl azodicarboxylate (DIAD) and triphenylphosphine.

5. The process of claim 3, wherein the first solvent in step 1) comprises tetrahydrofuran.

6. The process of claim 1, wherein step 2) comprises:
   2a) treating the mixture with an acid in a second solvent to provide the salt of the compound of formula VII; and
   2b) neutralizing the salt of the compound of formula VII with a second base in a third solvent comprising water to provide the compound of formula VII.

7. The process of claim 6, wherein the acid is an aqueous solution of HCl or methanesulfonic acid.

8. The process of claim 6, wherein the second solvent comprises toluene or isopropyl acetate.

9. The process of claim 6, wherein the second base is potassium carbonate.

10. The process of claim 1, wherein the ethyl 4-halobutyrate in step 3) is ethyl 4-bromobutyrate.

11. The process of claim 1, wherein the third base in step 3) is N,N-diisopropylethylamine.

12. The process of claim 1, wherein the fourth solvent in step 3) comprises dimethylacetamide.

13. The process of claim 1, wherein the fourth base in step 4) is sodium hydroxide.

14. The process of claim 1, wherein the fifth solvent in step 4) comprises ethanol and water.

15. The process of claim 1, wherein steps 1), 2a), and 2b) are conducted in one-pot.

16. The process of claim 2, wherein the compound of formula VI is used directly in step 2a) without isolation.

17. The process of claim 1, wherein steps 3) and 4) are conducted in one-pot.

18. A process for preparing a compound of formula VII:

(VII)

or a salt thereof, the process comprising:
1) contacting a compound of formula V:

(V)

with a compound of formula IV:

(IV)

and one or more coupling agents in a first solvent to form a mixture; and
2) treating the mixture with an acid to provide the compound of formula VII or the salt thereof,
wherein $R^1$ is hydrogen; and
$R^2$ and $R^3$ are independently hydrogen, substituted or unsubstituted $C_{1-8}$ alkyl, or substituted or unsubstituted $C_{6-12}$ aryl;
the one or more coupling agents in step 1) are a combination of diethyl azodicarboxylate (DEAD) and triphenylphosphine, a combination of diisopropyl azodicarboxylate (DIAD) and triphenylphosphine, a combination of tetraisopropylazodicarboxamide (TIPA) and triphenylphosphine, a combination of azodicarbonyldipiperidine (ADDP) and triphenylphosphine, or a combination of bis(2,2,2-trichloroethyl) azodicarboxylate (TCEAD) and triphenylphosphine; and
the first solvent in step 1) is dimethylformamide (DMF), dichloromethane (DCM), toluene, dimethylacetamide(DMAc), isopropyl acetate (IPAc), acetonitrile, tetrahydrofuran (THF), or mixtures thereof.

19. A process for preparing a compound of formula VII:

(VII)

or a salt thereof, the process comprising:
1) contacting a compound of formula V:

(V)

with a compound of formula IV:

(IV)

and a first base in a first solvent to form a mixture; and
2) treating the mixture with hydrochloric acid (HCl) to provide the compound of formula VII or the salt thereof,
wherein $R^1$ is methanesulfonate or p-toluenesulfonate;
$R^2$ is hydrogen; and
$R^3$ is substituted or unsubstituted $C_{6-12}$ aryl.

20. The process of claim 19, wherein $R^1$ is methanesulfonate, $R^2$ is hydrogen; and $R^3$ is phenyl.

21. The process of claim 19, wherein the first base is potassium carbonate.

22. The process of claim 19, wherein the first solvent comprises dimethylformamide.

* * * * *